United States Patent
Kendig et al.

(10) Patent No.: US 8,153,062 B2
(45) Date of Patent: Apr. 10, 2012

(54) ANALYTE DETECTION VIA ELECTROCHEMICALLY TRANSPORTED AND GENERATED REAGENT

(75) Inventors: Martin W. Kendig, Thousand Oaks, CA (US); Chuan-Hua Chen, Thousand Oaks, CA (US); D. Morgan Tench, Camarillo, CA (US); Jeffrey F. DeNatale, Thousand Oaks, CA (US); Frederick M. Discenzo, Brecksville, OH (US)

(73) Assignee: Teledyne Scientific & Imaging, LLC, Thousand Oaks, CA (US)

( * ) Notice: Subject to any disclaimer, the term of this patent is extended or adjusted under 35 U.S.C. 154(b) by 811 days.

(21) Appl. No.: 11/731,138

(22) Filed: Mar. 30, 2007

(65) Prior Publication Data

US 2008/0241932 A1  Oct. 2, 2008

(51) Int. Cl.
*G01N 15/06* (2006.01)

(52) U.S. Cl. ........ 422/68.1; 422/52; 422/25; 422/82.02; 422/82.03; 422/81; 422/420; 422/553; 204/403.09; 204/403.05; 204/408; 204/412; 436/526; 205/778; 429/191; 429/213

(58) Field of Classification Search .................. None
See application file for complete search history.

(56) References Cited

U.S. PATENT DOCUMENTS

| | | | | |
|---|---|---|---|---|
| 3,539,455 A | * | 11/1970 | Clark, Jr. | 205/778 |
| 4,430,397 A | * | 2/1984 | Untereker | 429/310 |
| 5,942,103 A | | 8/1999 | Wang et al. | 205/787 |
| 2003/0134426 A1 | * | 7/2003 | Jiang et al. | 436/121 |
| 2005/0221406 A1 | | 10/2005 | Arbab | |

FOREIGN PATENT DOCUMENTS

| WO | WO 98/28616 | * | 7/1998 |
|---|---|---|---|
| WO | WO 0202796 A2 | | 1/2002 |
| WO | WO 02069935 A1 | | 9/2002 |
| WO | WO 2005098427 A2 | | 10/2005 |

* cited by examiner

*Primary Examiner* — Sally Sakelaris
(74) *Attorney, Agent, or Firm* — Koppel, Patrick, Heybl & Philpott (57) ABSTRACT

Electrochemical devices, methods, and systems for detecting and quantifying analytes are disclosed. A chemical detection reagent is locally generated in a test solution by electrochemical reaction of a precursor compound caused to migrate into the test solution from a precursor solution separated from the test solution by a cell separator. This approach provides precise metering of the reagent, via the charge passed, and avoids the need to store a reagent solution that may be chemically unstable. In one embodiment, the starch concentration in a colloidal solution can be measured via spectroscopic detection of a blue complex formed by the interaction of starch with iodine produced, on demand, by electrochemical oxidation of iodide ion. The approach may also be used to characterize certain types of analytes. The invention is amenable to automation and is particularly useful for on-line monitoring of production processes, including the inclusion of feed back loop mechanisms for process control.

23 Claims, 3 Drawing Sheets

ANALYTE DETECTION VIA ELECTROCHEMICALLY TRANSPORTED AND GENERATED REAGENT

BACKGROUND OF THE INVENTION

1. Field of the Invention

This invention is generally concerned with analytical chemistry and, in particular, with the detection of starch in colloidal solution.

2. Description of the Related Art

Electrochemical reactions and techniques are widely used to detect chemical substances and to generate reagents for chemical detection and analyses. These approaches typically involve electrochemical oxidation of a precursor compound to generate a reagent capable of detecting a target analyte, and electrochemical cells with separate compartments have often been employed to generate a reagent from a precursor. In the amperiometric Karl-Fisher titration, for example, which is used to detect residual water in organic solvents, for example, an excess of iodide ion added to the test solution is electrochemically oxidized to iodine which, can react with other test solution components such that water is quantitatively consumed during the process (i.e. one mole of $I_2$ is consumed for each mole of water). The endpoint of the titration is the detection of excess iodine in the specimen, indicating that all of the water has been consumed. In order to avoid any back reduction of iodine, a separate test solution compartment is used for the cathode in this approach.

An excess of precursor is generally added to the solution used for reagent generation in these types of cells, which would be problematic in other applications. It is likely, for example, that a sensor based on the amperiometric Karl-Fisher titration could be developed for detecting the total water content in lubricating oils during service in engines, which is of significant interest to the transportation industry. However, addition of excess reagent precursor to the lubricant, which might degrade the lubricant properties, is undesirable. Furthermore, the presence of excess reagent is usually not a practical alternative since many types of reagents tend to undergo chemical decomposition during storage.

An example of a chemical analysis involving an unstable reagent is detection of starch by reaction with iodine. Starch is the major carbohydrate in plant tubers and seed endosperm, such as corn, wheat, potato, tapioca and rice, so that detection of starch is important to the food industry. Starch is an insoluble complex carbohydrate, a polymeric material having the chemical formula $(C_6H_{10}O_5)_n$ and consisting of various portions of two glucose polymers, amylase and amylopectin. In water, starch usually forms colloidal solutions that turn from a translucent white color to deep blue in the presence of atomic iodine, which adsorbs on the suspended starch colloidal particles to form a starch-iodine complex. The resulting blue-colored starch-iodine complex absorbs light in the wavelength range from about 400 to 800 nm, with a peak (maximum) absorbance for this complex at about 580 nm. In addition, the light absorbance of the complex is proportional to the concentration of starch in solution and the reaction is an extremely specific marker for starch (and potentially for starch analogs or derivatives). Once the available starch is completely complexed with iodine (starch-$I_2$), any further addition of iodine ($I_2$), which is insoluble aqueous solution, usually results in the formation triiodide ion ($I_3^-$) which typically imparts a brown color to an aqueous test solution.

A standard method for determining the starch concentration in a colloidal solution is to add an excess of iodine (as a reagent solution) to the colloidal solution and then measure the light absorbance of the resulting test solution at 580 nm. This spectroscopic approach has the disadvantage that the iodine reagent solution is unstable under ambient conditions and must be periodically replaced. This generates an appreciable waste stream, which is exacerbated by the relatively large volume of the iodine reagent needed for the analysis.

For some applications, delivery of the iodine reagent solution can also be problematic, especially for automated on-line analysis. There is, for example, a need for on-line detection of starch in rinse water from sliced potatoes used to manufacture potato chips. A sharp slicing blade is required to provide potato slices of uniform thickness and high quality, but the lifetime of the blade varies. In addition to degrading product quality, a dull slicing blade tends to increase damage to potato cells, which releases starch. An on-line method for monitoring starch in rinse water from the potato slicing operation would enable slicing blades to be changed as needed so as to optimize potato chip quality and blade usage. Early detection of blade degradation would enable blades to be changed at a convenient time to minimize process disruption, saving labor and material costs. Another potential application for on-line starch monitoring is to track the hydrolysis of starch into cyclodextrins. This conversion process, often initiated by readily available enzymes, has application in the food, cosmetic, pharmaceutical, agricultural, environmental, and chemical industries. Monitoring the conversion of starch to cyclodextrins can insure the reaction is complete under various processing conditions and with minimum enzyme consumption. A further application for controlled initiation and monitoring starch-iodide complex is to monitor phosphites in groundwater Therefore, a method for local injection of a detection reagent provided on demand by a stable reagent precursor reservoir would be advantageous in many analyte detection or analysis applications, particularly where reagents undergo chemical decomposition during storage and where waste stream management or on-line implementation are desirable.

SUMMARY OF THE INVENTION

The present invention provides devices, methods, and systems for detecting an analyte in a test solution by locally generating a chemical detection reagent in a test solution, and systems containing such devices. The detection reagent is generated via electrochemical reaction of a reagent precursor compound which, on demand, can migrate into the test solution from a precursor solution contained in separate precursor solution compartment. The migration is initiated, and the reagent generated, by the application of electrical power to the device. The controlled release of reagent is localized in the test solution, and the quantity of reagent generated is dependent upon the amount of power applied. Systems containing the device can provide additional advantages such as automated detection and quantification of analyte, periodic detection and reaction trending, optimum use of reagents and minimum fluid waste.

The device of the invention includes an electrochemical cell that includes a test solution compartment having a test solution, a precursor solution compartment having a precursor solution, a cell separator between the precursor and test solution compartments, a first electrode in contact with the test solution, a second electrode in contact with the precursor solution, and an electrical power source electrically connected across the first electrode and the second electrode. In the absence of electrical power, the cell separator inhibits precursor and test solution mixing. However, when electrical power is applied to the first electrode and the second electrode of the device, the cell separator permits transfer of the precursor compound from the precursor solution to the test solution, where it reacts electrochemically to generate a reagent for detecting an analyte. The device can be used in conjunction with other systems such as those capable of transporting, detecting and/or quantifying the analyte.

In the method of the invention, a quantity of electrical power from an electrical power source is applied between the first electrode and the second electrode, which causes at least some of the precursor compound in the precursor solution to migrate through the cell separator to the test solution and electrochemically react at the first electrode to generate the reagent.

The present invention provides significant advantages compared to the prior art. In particular, the invention enables a reagent to be generated as-needed and in a small, localized volume. Electrochemical generation provides precise metering of the reagent, via the charge passed, and avoids the need to store a reagent solution, which may be chemically unstable under ambient conditions. The waste stream generated by the analysis of the invention is minimized by precise localized reagent generation, and elimination of the need for an unstable reagent solution. The invention is also amenable to automation and is particularly useful for on-line monitoring of production processes. The invention may also be used in a microfluidic device of the type used for "lab-on-a-chip" analysis, particularly with respect to quantifying amounts of analytes in test solutions. In this case, the capability of localized delivery of precise amounts of the reagent, which is provided by the invention, is especially useful. For example, the degree of color change with the controlled release of prescribed amounts of reagent can enable more precise quantification of the analyte.

Further features and advantages of the invention will be apparent to those skilled in the art from the following detailed description, taken together with the accompanying drawings.

BRIEF DESCRIPTION OF THE DRAWINGS

These figures are not to scale and some features have been enlarged for better depiction of the features and operation of the invention.

DETAILED DESCRIPTION OF THE INVENTION

The present invention provides devices, methods, and systems for detecting and quantifying an analyte in a test solution by locally generating a chemical detection reagent in the test solution via electrochemical reaction of a precursor compound caused to migrate into the test solution from a precursor solution contained in separate precursor solution compartment, where it reacts electrochemically to form a reagent for detecting a target analyte. The systems generally include an electrochemical cell with a test solution compartment and a precursor solution compartment separated by a cell separator which, in the absence of electrical power, inhibits mixing between the precursor and test solutions. The analyte in the test solution can be detected by any suitable means, including visual inspection and the use of optical detection systems.

Other features and advantages of the invention will be apparent from the following detailed description when taken together with the drawings, and from the claims. The following description presents preferred embodiments of the invention representing the best mode contemplated for practicing the invention. This description is not to be taken in a limiting sense but is made merely for the purpose of describing the general principles of the invention whose scope is defined by the appended claims.

Before addressing details of embodiments described below, some terms are defined or clarified. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of the "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The following definitions refer to the particular embodiments described herein and are not to be taken as limiting; the invention includes equivalents for other undescribed embodiments. Technical terms used in this document are generally known to those skilled in the art. The term "solution" encompasses both solutions of dissolved substances and colloidal solutions containing suspended particles. Colloidal solutions may also contain dissolved substances. The symbol "M" means molar concentration. Calibration data are typically handled as calibration curves or plots but such data may be tabulated and used directly, especially by a computer, and the terms "curve" or "plot" include tabulated data. The term "plastic" encompasses synthetic and semi-synthetic materials that contain one or more organic polymeric substances having large molecular weight as an essential ingredient, are solid in their finished state, and which, at some stage in their manufacture or processing into finished articles, can be shaped by flow. Plastics may also contain other substances to improve performance or economics. The term "porous" encompasses materials possessing or full of pores, vessels, or holes, or which are otherwise capable of being penetrated.

Attention is now directed to more specific details of embodiments that illustrate but not limit the invention.

The present invention provides devices, methods, and systems for detecting, quantifying and analyzing an analyte in a test solution by locally generating a chemical detection reagent in the test solution via electrochemical reaction of a precursor compound which can migrate into the test solution from a separate precursor solution compartment. In particular, the systems of the present invention can include: (1) a test solution compartment containing the test solution; (2) a precursor solution compartment containing a precursor solution having a regent precursor; (3) a cell separator between the test solution compartment and the precursor solution compartment which, in the absence of electrical power, inhibits solution mixing (including migration of reagent precursor compound); (4) a first electrode in contact with the test solution; (5) a second electrode in contact with the precursor solution; and (6) an electrical power source electrically connected across the first electrode and the second electrode. In one method of the invention, electrical power can be applied between the first electrode and the second electrode so as to cause at least some of the precursor compound to migrate through the cell separator from the precursor solution to the test solution and electrochemically react to generate a reagent. A system according to the invention may include an optical detection system capable of detecting the absorption spectrum of a light source. The optical response may, for example, be correlated with the release of a controlled amount of precursor compound to establish a more accurate means to detect or quantify the analyte.

The precursor compartment and the test solution compartment may be fabricated from any suitable electrically insulating material, including without limitation those selected from the group consisting of glasses, plastics, and combinations thereof. Corrosion resistant metals, stainless steel, for example, may similarly be used to fabricate portions of these compartments not requiring electrical insulation (e.g. to avoid shorting out the electrodes) or optical transparency (to permit measurement of the light absorbance of the test solution).

The cell separator may contain any suitable material and configuration that allows electromigration of the precursor compound but inhibits mixing of the precursor solution and the test solution. Suitable cell separator materials include without limitation semi-permeable polymer membranes as well as other porous materials such as ceramics (alumina, for example), glasses (nanoporous silica, for example), polysilicon, and plastic materials. A preferred cell separator configuration is a disk or rod sealed inside the end of an insulating tube via heat shrinking the tube, or via use of an o-ring or compression fitting.

The first and second electrodes may contain any suitable conductive or semi-conductive material. Anode materials preferably resist electrochemical oxidation. A preferred anode material is a noble metal selected from the group consisting of platinum, iridium, osmium, palladium, rhenium, rhodium, ruthenium, and alloys thereof. Other suitable anode materials include without limitation stainless steels, conducting or semiconducting metal oxides (nickel oxide, for example). and graphite (and other forms of carbon). Although cathode materials need not be resistant to oxidation, the same materials used for anodes may also be used for cathodes.

The first electrode may be of any suitable configuration providing sufficient contact between the electrochemically generated reagent and the test solution. The first electrode can be preferably disposed upon, in contact with, or in close proximity to at least a portion of the cell separator so as to efficiently generate the reactant from the precursor compound that migrates through the cell separator. Suitable first electrode configurations include without limitation a mesh, a porous foil, or a porous deposit on the cell separator, for example.

The device of the invention may further contain a transport system for causing the test solution to flow from a test solution source to the electrochemical cell, from the electrochemical cell to an analyte detection/measurement cell, or both. The test solution source may be any source capable of providing test solution, including without limitation a process that generates the test solution, for example, so as to provide real-time monitoring of the process. The test solution may be caused to flow by a mechanical pump, hydraulic pressure, gas pressure, gravity feed, or any other suitable means. A preferred means of causing test solution flow is a mechanical pump.

The device of the invention may also contain a detection system for detecting the analyte, including without limitation an optical detection system. One preferred optical detection system includes a light source, an optical cell and a light detector. The device of the invention can further include a measurement system for analyzing the analyte detected by the device, including without limitation determining the quantity or type of one or more analytes in the test solution. In one preferred embodiment, the amount of analyte can be quantified by measuring the light absorbance of the test solution. In another preferred embodiment, the type of analyte detected by the device can be characterized (e.g. identified or characterized as a belonging to a particular group or sub-group) or otherwise analyzed by measuring the light absorbance at a wavelength which is characteristic for that particular analyte.

Electromigration of the reagent precursor from the precursor solution to the test solution can be achieved using a number of suitable device technologies, including without limitation electrophoresis and electroosmosis (e.g. a microfluidic device). Suitable microfluidic devices can include capabilities for flow and one-way valves.

The method of the invention for detecting an analyte in a test solution includes the steps of: (1) providing an electrochemical cell containing a first electrode in contact with a test solution in a test solution compartment, a second electrode in contact with a precursor solution containing a precursor compound in a precursor compartment, and a cell separator between the test solution compartment and the precursor compartment that inhibits solution mixing but which, upon application of electrical power, permits transfer of the precursor compound from the precursor solution to the test solution; (2) applying a quantity of electrical power between the first electrode and the second electrode so as to cause at least some of the precursor compound to migrate through the cell separator and electrochemically react at the first electrode to generate a reagent.

The method of the invention may further include systems for: (3) causing the test solution to flow from a test solution source to the electrochemical cell, from the electrochemical cell to an analyte detection/measurement cell, or both; (4) detecting the analyte; or (5) quantifying the amount of analyte (e.g. determining the concentration of analyte). Analyte detection can be achieved by any suitable means, including without limitation visual inspection and optical techniques such as the measurement of light absorbance. Suitable wavelengths for optical measurements will typically depend upon the nature of the analyte or sample and, in some cases, it may be necessary to take measurements at more than one wavelength to obtain accurate results (e.g. analytes having multiple wavelength maxima or samples in which one or more absorbance maxima are obscured by interference from other materials or compounds in the test solution).

The present invention is useful for a wide variety of analytical applications. One embodiment provides a method and a device for quantifying the starch concentration in a test solution. This embodiment is described below in detail for illustrative purposes but should not be considered indicative of the scope of the invention.

A device of the invention for analyzing the starch concentration in a test solution can include: (1) a test solution compartment containing the test solution; (2) a precursor solution compartment containing a precursor solution containing iodide ion; (3) a cell separator between the test solution compartment and the precursor solution compartment that inhibits solution mixing but permits transfer of iodide ion from the precursor solution to the test solution when power is applied to the device; (4) an anode in contact with the test solution; (5) a cathode in contact with the precursor solution; (6) an electrical power source electrically connected across the anode and the cathode; and (7) a system for measuring the light absorbance of the test solution at one or more wavelengths, such as a system having a light source, an optical cell and a light detector. The wavelength used for detection will typically depend upon the absorbance spectrum of the target analyte. In the method of the invention for analyzing the starch concentration in a test solution, electrical power can be applied between the anode and cathode so as to cause iodide ion to migrate through the cell separator from the precursor solution to the test solution and be oxidized at the anode to iodine, which combines with starch in the test solution to produce a starch-iodine complex that absorbs radiation within a particular wavelength range. A typical starch-iodine complex, for example, absorbs light in a wavelength range of about 400 nm to about 800 nm, with a maximum absorbance at around 580 nm. There may be applications or conditions which warrant optical measurements at more than one wavelength, including samples in which one or more absorbance maxima are obscured by interference from other materials or compounds in the test solution.

Iodide ion may be added to the precursor solution as an iodide salt containing any suitable cation, including without limitation metal cations and alkylammonium cations. Suitable iodide salts include without limitation sodium iodide, potassium iodide and tetraalkylammonium iodide. The iodide ion concentration may be any suitable value (which may be limited only by the solubility of the iodide salt used). The concentration of iodide ion in the precursor solution is preferably within the range from 0.01 to 1.0 M.

One non limiting method for measuring the light absorbance of the test solution at a particular light wavelength can include a light source, an optical cell, and a light detector. Spectroscopic equipment is commercially available for measuring solution absorbance at a wide range of predetermined wavelengths. The electrochemical cell used to generate iodine may be integrated with the optical cell used to measure the light absorbance of the test solution.

One method for quantifying starch according to the invention is to determine the starch concentration in a test solution by: (1) providing an electrochemical cell containing an anode in contact with a test solution in a test solution compartment, a cathode in contact with a precursor solution containing iodide ion in a precursor solution compartment, and a cell separator between the test solution compartment and the precursor solution compartment that inhibits solution mixing but permits transfer of iodide ion from the precursor solution to the test solution when power is applied to the cell; (2) applying a quantity of electrical power between the anode and the cathode so as to cause at least some of the iodide ion to migrate through the cell separator and be oxidized at the anode to iodine; (3) measuring the light absorbance at one or more wavelengths for a portion of the test solution containing the iodine; (4) generating a calibration curve by repeating Steps (1)-(3) for a plurality of calibration solutions of known starch concentrations, in place of the test solution; and (5) comparing the absorbance of the test solution with the calibration curve to determine the concentration of starch in the test solution. The starch in the test solution adsorbs a fraction of the iodine generated to produce a blue starch-iodine complex that absorbs light over the wavelength range from about 400 to 800 nm, and typically exhibits a light absorption peak centered at a wavelength of 580 nm. Light absorbance in this wavelength range, preferably at or near 580 nm, can then be measured for the test solution containing the starch-iodine complex. A calibration curve can be generated by repeating this procedure for a plurality of calibration solutions of known starch concentrations, in place of the test solution. The starch concentration of the test solution can be determined by comparing the absorbance measured for the test solution with the calibration curve. The same calibration curve can be used for analysis of a plurality of test solutions.

Preferably, sufficient iodine can be generated electrochemically to form the starch-iodine complex with substantially all of the starch in the portion of the test solution used for the optical absorbance measurement. In this case, highest accuracy can be provided since the optical absorbance is limited by the starch concentration and not by the iodine concentration. Nonetheless, acceptable accuracy for the starch analysis may be attained for some applications via steady-state generation of iodine whose concentration may be insufficient to fully convert the starch in the test solution to the starch-iodine complex. Additionally, the controlled, slow release of iodide may be introduced into a flow stream of fluid. The flow stream may be implemented as a bypass flow or normal fluid flow stream. Downstream from the release of iodide in the flow stream may be a source-detector pair that continually monitors the absorbance of light in the range of 400 to 800 nm, and particularly at 580 nm.

The quantity of iodine generated by oxidation of iodide ion according to the invention may be controlled via the electrical power applied across the anode and cathode of the invention. The quantity of iodine generated is directly proportional to the charge passed. Any suitable waveform of applied voltage or current may be used. The amount of power required for a particular application may be predetermined for any particular analyte concentration range using standard power v $I_2$ calibration techniques. A preferred approach for generating a predetermined amount of iodine can be to apply a constant current for a predetermined time (current×time=charge). Alternatively, a constant voltage may be applied and the resulting current integrated to yield the charge. A preferred approach for generating iodine at a constant rate, which can be appropriate for measurements according to the invention involving a continuously flowing test solution, is to apply a constant current. In this case, the rate of iodine generation is directly proportional to the magnitude of the current. A constant applied voltage may also be used but the current, which determines the rate of iodine generation, may not be constant in this case.

The iodine generated can be detected by several techniques, including without limitation visual detection (e.g. by a person operating or nearby the system) of the iodine's characteristic blue color in solution and optical detection at one or more wavelengths. The quantity of iodine generated by oxidation of iodide ion according to the invention may be determined using a number of approaches, including without limitation manually for any one particular test solution, as outlined above in steps (3)-(5), or adapted for automated analysis. One non-limiting method of the invention for quantifying the amount of starch in the test solution and, in particular, for determining the starch concentration in a test solution, may further include the step of: (6) causing the test solution to flow from a test solution source to the electrochemical cell, from the electrochemical cell to the optical cell, or both. For example, a test solution may be caused to flow from the test solution source to the electrochemical cell so as to monitor the starch concentration generated by an industrial process. The test solution may be caused to flow continuously, periodically or intermittently, and at a constant rate or a variable rate. For example, test solution may be caused to periodically flow so as to sequentially: (1) transport a portion of test solution to be analyzed from the test solution source to the electrochemical cell; (2) allow enough time for sufficient iodine to be generated to form the starch-iodine complex with substantially all of the starch in the portion of the test solution to be analyzed; and (3) transport the portion of the test solution containing the starch-iodine complex to the optical cell. Note that solution flow could also be stopped or slowed to allow time for making the optical absorbance measurements but this should not be necessary typically since such optical measurements can be made quickly.

Alternatively, the test solution may be caused to flow at a constant rate that may be sufficiently slow to allow generation of sufficient iodine to react with the starch in the flowing test solution. A constant test solution flow rate enables the starch concentration in the test solution source to be continuously monitored in real time, except for the delay involved in transporting the test solution from the source to the electrochemical cell. This delay may be minimized by alternating between fast flow to transport the test solution from the source to the electrochemical cell, and slower flow to transport the test solution through the electrochemical cell during iodine generation.

It may be advisable to put several optical detectors separated by a known distance downstream from the iodine release location. Knowing the flow rate and separation distance, it should be possible to estimate the reaction rate and therefore estimate the starch concentration. This estimate may be made quickly and before all starch has been converted to a starch iodide complex. An alternative method can be to monitor the release of iodine into the starch solution, such as by recording the electrochemical cell current, voltage, and time. The absorbance of light in the 400 to 800 nm range, and particularly at 580 nm, may be simultaneously monitored to detect analyte when there is no additional color change or change in absorbance. The amount of iodine released to achieve this state may be used to compute the amount (i.e. concentration) of starch that was converted with this known amount of iodine. Yet another technique can be to provide the controlled release of another fluid, such as an enzyme that converts the starch to sugar. The amount of sugar (e.g. glucose) in the test solution may indicate the amount of starch present. The amount of sugar present may be detected, for example, using another electrochemical cell with electrodes immersed in the test fluid. Yet another option can be to provide the controlled release of an enzyme and a precursor fluid such as iodide. The resulting measurement of the starch-iodide complex (such as via light absorbance) and sugar content (such as via an electrochemical cell) may provide a very accurate measurement of the quantity of starch detected (e.g. through calibration with test solutions containing known quantities of starch) and potentially characterize the type of starch(s) present (e.g. where the wavelength, intensity, or other property of light absorbed is dependent upon the type of starch present). Multiple precursor solutions may be added to improve the accuracy of starch detection and quantification, to reduce the time required for analysis, or to minimize the amount of test fluids required. Such precursor solutions may include a clarifying agent or a precipitating agent to provide better visual indication of the absorbance, preferably in the 400-800 nm wavelength range.

Automated analysis of the types described above could also include analyte sensors for controlling real time online processes such as, for example, a feedback loop mechanism to sense and compensate for dull blades in a potato processing plant in real time. Feedback loops for process control could also be used for many other purposes, including without limitation a feedback loop used to control temperature and reaction times in order to ensure that a hydrolysis reaction has completed.

The embodiments and examples set forth herein were presented to explain the nature of the present invention and its practical application, and thereby to enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims. For example, while a single electrochemical cell activated at one power level can detect or analyze an analyte, the invention contemplated is not so limited. One skilled in the art will recognize that the number, dimensions, structure, or configuration of device components may vary and accordingly are not to be construed as limiting the scope of the invention. Devices containing multiple precursor solution compartments, test solution compartments, and electrode pairs could be used to detect or analyze a number of analytes sequentially or simultaneously. Similarly, depending upon the nature of the cell separator, electromigration of the precursor compound could be achieved by electrophoretic or electroosmotic mechanisms.

EXAMPLES

Example 1

Figures 1A, 1B:
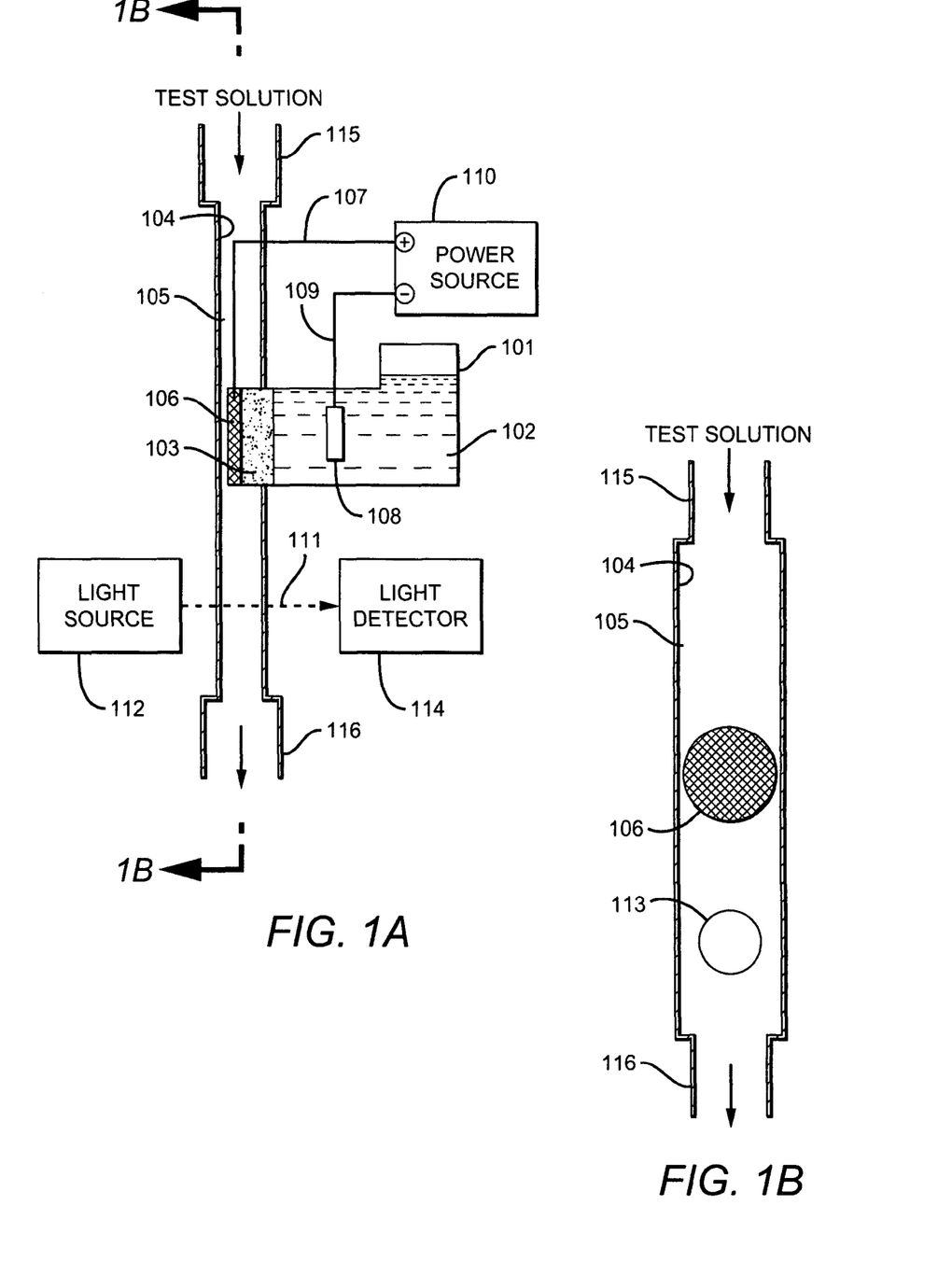
FIG. 1A illustrates a schematic section view of one embodiment of the device of the invention suitable for starch analysis which includes a planar flow-through cell used for both iodine generation and test solution absorbance measurements via transmitted light.
FIG. 1B illustrates a schematic cross section view of the embodiment shown in FIG. 1A illustrating the porous cell separator and light beam path within the flow-through cell.

FIGS. 1A and 1B illustrates front and side views, respectively, of one embodiment of the device of the invention where a planar flow-through cell is used for both iodine generation and test solution absorbance measurements via transmitted light. A precursor compartment 101 containing a precursor solution 102 (containing iodide ion) is connected via a cell separator 103 to a test solution compartment 104 containing a test solution 105 which may contain starch. An anode 106 is in contact with test solution 105 and is electrically connected via a wire 107 to the positive terminal of a power source 110. Anode 106 is in the form of a wire mesh disposed upon, in contact with, or in close proximity to cell separator 106. A cathode 108 is in contact with precursor solution 102 and is electrically connected via a wire 109 to the negative terminal of power source 110. Test solution compartment 104 is preferably made glass and has a rectangular cross section with flat parallel sides suitable for optical absorbance measurements. In this case, the test solution compartment 104 may serve as both an electrochemical cell and an optical cell. Optical absorbance measurements are performed via a light beam 111, which is generated by a light source 112, passes through test solution compartment 104 and test solution 105 at an optical detection spot 113, and is detected by a light detector 114.

For the embodiment of FIG. 1, measurements are made by causing test solution 105 to flow (as indicated by the arrows) from a source (not shown) via an inlet tube 115, through test solution compartment 104, and from test solution compartment 104 via outlet tube 116. Electrical power applied between anode 106 and cathode 108 causes iodide ion to migrate through cell separator 103 from precursor solution 102 to test solution 105 and be oxidized at anode 106 to iodine, which combines with any starch in the test solution 105 to produce a starch-iodine complex that absorbs light over the wavelength range from about 400 to 800 nm. Test solution 105 containing the starch-iodine complex is swept by the solution flow to optical detection spot 113 where the optical absorbance is measured in this wavelength range, preferably at or near the peak absorbance wavelength (580 nm), to determine the starch concentration in test solution 105. Preferably, the separation distance between anode 106 and the inside wall of test solution compartment 104 is sufficiently small to ensure that the iodine generated at anode 106 efficiently adsorbs on the starch in test solution 105. Restricted flow or baffling may be used in the region between the electrochemical cell and the optical cell to enhance solution mixing, to ensure good contact between the iodine and the starch. For example, the width of test solution compartment 104 could be reduced in this region.

Example 2

Figure 2:
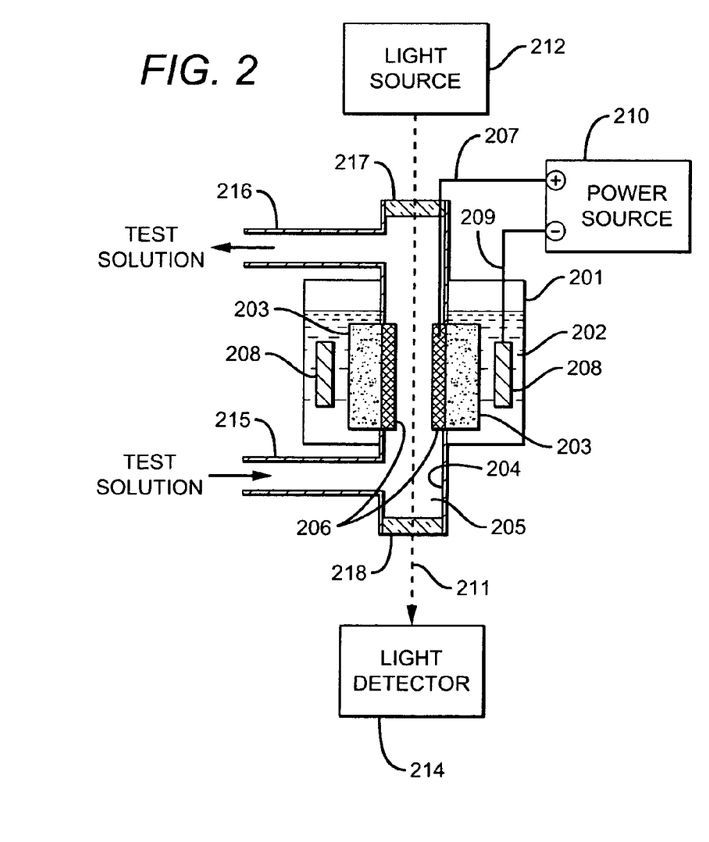
FIG. 2 illustrates a schematic section view of one embodiment of a device of the present invention suitable for starch analysis, including a cylindrical flow-through cell used for both iodine generation and test solution absorbance measurements via transmitted light.

FIG. 2 illustrates another embodiment of the device of the invention where a cylindrical flow-through cell is used for both iodine generation and test solution absorbance measurements via transmitted light. A cylindrical precursor solution compartment 201 containing a precursor solution 202 (containing iodide ion) is connected via a concentrically cylindrical cell separator 203 to a concentrically cylindrical test solution compartment 204 containing a test solution 205. A concentric cylindrical anode 206 is in contact with test solution 205 and is electrically connected via a wire 209 to the positive terminal of a power source 210. Anode 206 is in the form of a concentrically cylindrical wire mesh disposed upon, in contact with, or in close proximity to cell separator 203. A concentrically cylindrical cathode 208 is in contact with precursor solution 202 and is electrically connected via a wire 209 to the negative terminal of power source 210. Cylindrical test solution compartment 204 is preferably made glass and has parallel optical windows 217 and 218 (suitable for optical absorbance measurements) at each end of the glass cylinder. In this case, test solution compartment 204 may serve as both an electrochemical cell and an optical cell. Optical absorbance measurements are performed via a light beam 211, which is generated by a light source 212, passes approximately along the axis of test solution compartment 204 (through optical window 217, test solution 205, and optical window 218, and is detected by a light detector 214.

For the embodiment of FIG. 2, measurements are made by causing test solution 205 which may contain starch to flow (as indicated by the arrows) from a source (not shown) via an inlet tube 215, through test solution compartment 204, and from test solution compartment 204 via outlet tube 216. Electrical power applied between anode 206 and cathode 208 causes iodide ion to migrate through cell separator 203 from precursor solution 202 to test solution 205 and be oxidized at anode 206 to iodine, which combines with starch in test solution 205 to produce a starch-iodine complex that absorbs light over the wavelength range from about 400 to 800 nm. The optical absorbance of test solution 205 is measured in this wavelength range, preferably at or near the peak absorbance wavelength (580 nm), to determine the starch concentration in the test solution. This embodiment is particularly well suited for continuously monitoring the starch concentration in a test solution. The diameter of test solution compartment 204 is preferably sufficiently small that the iodine is generated as close as practical to optical beam 211 to provide efficient adsorption of the iodine on the starch in test solution 205.

Example 3

Figure 3:
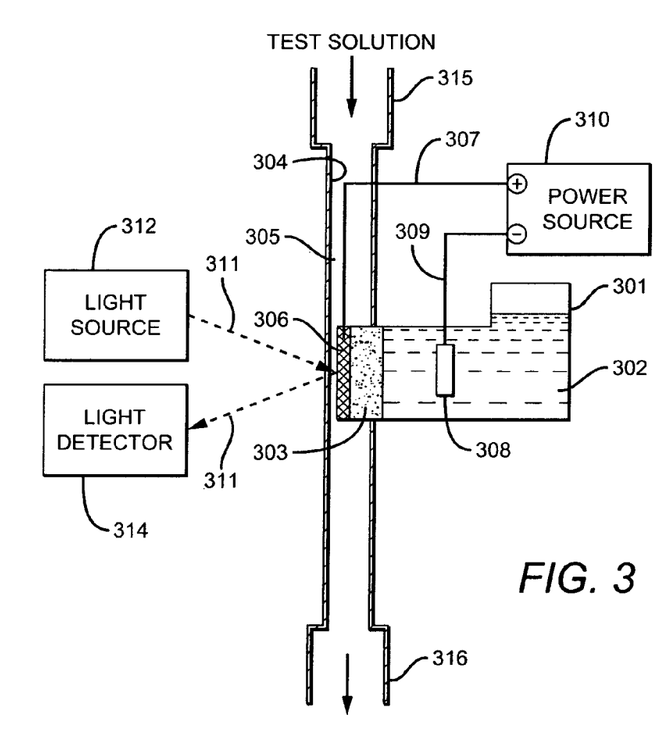
FIG. 3 illustrates a schematic section view of one embodiment of the device of the present invention for starch analysis, including a planar flow-through cell used for both iodine generation and test solution absorbance measurements via reflected light.

FIG. 3 illustrates yet another embodiment of the device of the invention where a planar flow-through cell is used for both iodine generation and test solution absorbance measurements via reflected light. A precursor solution compartment 301 containing a precursor solution 302 (containing iodide ion) is connected via a cell separator 303 to a test solution compartment 304 containing a test solution 305 which may contain starch. An anode 306 is in contact with test solution 305 and is electrically connected via a wire 307 to the positive terminal of a power source 310. In this embodiment, anode 306 is preferably in the form of a reflective metal layer disposed upon, in contact with, or in close proximity to cell separator 306. In order to allow iodide ions to reach the outer surface of anode 306, the reflective metal layer may have sufficient microporosity, or may be a grid or perforated foil with sufficient reflective surface area. A cathode 308 is in contact with precursor solution 302 and is electrically connected via a wire 309 to the negative terminal of power source 310. Test solution compartment 304 is preferably made glass and has a rectangular cross section with flat parallel sides suitable for optical absorbance measurements. In this case, test solution compartment 304 may serve as both an electrochemical cell and an optical cell. Optical absorbance measurements are performed via a light beam 311, which is generated by a light source 312 and is reflected from anode 306, passing through one side of test compartment 304 and test solution 305, before being detected by a light detector 314.

For the embodiment of FIG. 3, measurements can be made by causing test solution 305 to flow (as indicated by the arrows) from a source (not shown) via an inlet tube 315, through test solution compartment 304, and from test solution compartment 304 via outlet tube 316. Electrical power applied between anode 306 and cathode 308 causes iodide ion to migrate through cell separator 303 from precursor solution 302 to test solution 305 and be oxidized at anode 306 to iodine, which combines with starch in test solution 305 to produce a starch-iodine complex that absorbs light over the wavelength range from about 400 to 800 nm. The optical absorbance of test solution 305 is measured in this wavelength range, preferably at or near the peak absorbance wavelength (580 nm), to determine the starch concentration in the test solution. Preferably, the separation distance between anode 306 and the inside wall of test solution compartment 304 is sufficiently small to ensure that the iodine generated at anode 306 efficiently adsorbs on the starch in test solution 305.

Example 4

Figure 4:
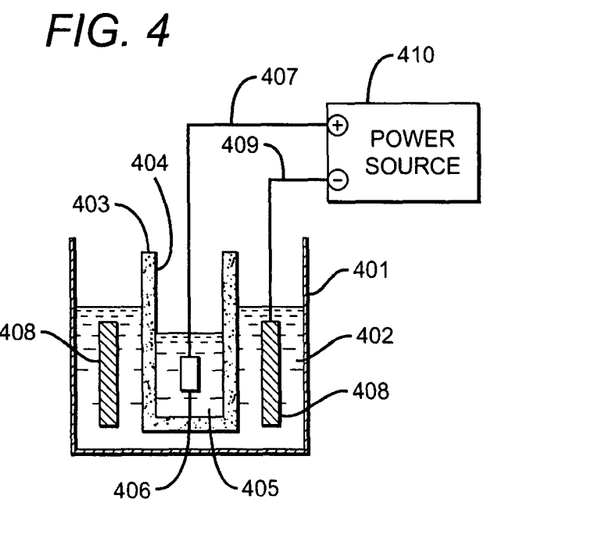
FIG. 4 illustrates a schematic section view of one type of electrochemical cell of the present invention used to demonstrate the efficacy of the invention for starch analysis.

The efficacy of the invention was demonstrated by electrochemically generating iodine in a series of standard solutions containing various known concentrations of starch, and obtaining a linear relationship between the light absorbance at 580 nm and the starch concentration. FIG. 4 illustrates the electrochemical cell used for this demonstration. A 250-mL glass beaker 401 containing precursor solution 402 (0.1 M potassium iodide) served as the precursor solution compartment. The test solution compartment 404 was a porous porcelain crucible 403 (CoorsTek Part No. 60493, available from CoorsTek, Inc., Golden, Colo.) containing 20 ml of test solution 405, which contained various known concentrations of starch. Porcelain crucible 403, which served as the cell separator, had a wall thickness of 4.4 mm and 38.5% apparent porosity with a pore size of <0.5 µm and a bubbling pressure of >80 psi. The anode 406 was a piece of platinum foil (surface area 1.21 $cm^2$), which was spot welded to a platinum wire. Anode 406 was immersed in test solution 405 and was electrically connected via a wire 407 to the positive terminal of a power source 410 (Hewlett-Packard HP6654A power supply). A cylindrical platinized titanium mesh cathode 408 was positioned around crucible 403 in precursor solution 402 and was electrically connected via a wire 409 to the negative terminal of power source 410. A constant voltage of 30 volts was applied for 30 seconds to generate iodine for each test solution. In all cases, the current tended to increase from 160 to 240 mA with time, presumably due to reduced electrical resistance as iodide ion accumulated in the test solution. This current variation did not affect the results since the charge passed (about 6 coulombs) provided sufficient iodine to react with substantially all of the starch in the test solution. Test solutions from the electrochemical cell were stirred, and the absorbance was measured externally using a polystyrene cuvette optical cell (1.0 cm path length) and an Ocean Optics S2000 miniature fiber optic spectrometer.

Figure 5:
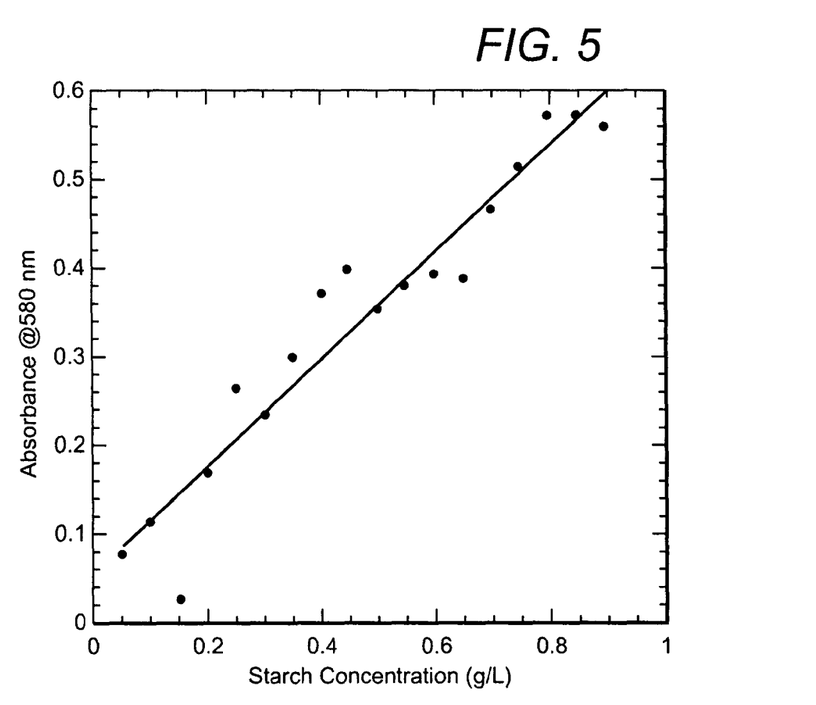
FIG. 5 is a plot of light absorbance at 580 nm as a function of starch concentration in solutions in which iodine was electrochemically generated using an electrochemical cell according to the embodiment shown in FIG. 4.

FIG. 5 shows a plot of light absorbance at 580 nm as a function of starch concentration in solutions in which iodine was electrochemically generated using the electrochemical cell illustrated in FIG. 4. Good linearity for this plot is evident.

Several embodiments of the present invention have been illustrated and described above. Modifications and additional embodiments, however, will undoubtedly be apparent to those skilled in the art. Furthermore, equivalent elements may be substituted for those illustrated and described herein, parts or connections might be reversed or otherwise interchanged, and certain features of the invention may be utilized independently of other features. Consequently, the exemplary embodiments should be considered illustrative, rather than inclusive, while the appended claims are more indicative of the full scope of the invention.

We claim:
1. An analyte detecting device, comprising:
    at least one test solution compartment comprising a test solution, wherein the test solution comprises at least one analyte;
    at least one precursor solution compartment comprising a precursor solution, wherein the precursor solution comprises at least one reagent precursor compound;
    at least one first electrode in contact with the test solution in the at least one test solution compartment;
    at least one second electrode in contact with the precursor solution in the at least one precursor solution compartment; and
    at least one electrical power source electrically connected across the at least one first electrode and the at least one second electrode; and
    at least one cell separator between the at least one test solution compartment and the at least one precursor solution compartment, wherein the permeability of the at least one cell separator increases upon application of at least one quantity of electrical power between the at least one first electrode and the at least one second electrode.
2. The device of claim 1,
    wherein the device is activated by an application of at least one quantity of electrical power between the at least one first electrode and the at least one second electrode, and the at least one separator inhibits mixing of the test solution and the precursor solution when the device is inactive; and
    activation of the device permits at least some of the at least one reagent precursor compound to migrate from the precursor solution, through the at least one cell separator, and into the test solution, thereby generating a reagent which reacts with the at least one analyte.
3. The device of claim 1, wherein the cell separator comprises at least one porous material selected from the group consisting of semipermeable membranes, ceramics, glasses, plastics, silicon, polysilicon, and combinations thereof.
4. The device of claim 1, wherein the device comprises at least one of an electrochemical cell and a microfluidic device.
5. The device of claim 4, wherein the at least one microfluidic device includes at least one valve selected from the group consisting of a flow valve, a one-way valve, and combinations thereof.
6. The device of claim 1, wherein at least one of the at least one first electrode and the at least one second electrode comprises a noble metal selected from the group consisting of platinum, iridium, osmium, palladium, rhenium, rhodium, ruthenium, and combinations thereof.
7. The device of claim 1, further comprising a transport system arranged to transport at least one portion of the test solution from a test solution source to the at least one test solution compartment, from the at least one test solution compartment to an analyte detection system, or both.
8. The device of claim 1, further comprising an analyte detection system arranged to detect the analyte after it reacts with the reagent.
9. The device of claim 8, wherein the detection system is an optical detection system.
10. The device of claim 9, wherein the optical detection system comprises a light source, an optical cell and a light detector.
11. The device of claim 8, further comprising a measurement system arranged to quantify the amount of analyte detected by the device.
12. The device of claim 11, wherein the amount of analyte is quantified by measuring the light absorbance of the test solution.

13. The device of claim 8, further comprising an analytic system arranged to characterize the analyte detected by the device.

14. A starch detecting device, comprising:
- a test solution compartment comprising a test solution, wherein the test solution comprises starch;
- a precursor solution compartment comprising a reagent precursor solution, wherein the precursor solution comprises iodide ions;
- an anode in contact with the test solution;
- a cathode in contact with the precursor solution; and
- an electrical power source electrically connected across the anode and the cathode; and
- a cell separator between the test solution compartment and the precursor solution compartment, wherein the permeability of the separator increases upon application of at least one quantity of electrical power between the anode and the cathode.

15. The device of claim 14, wherein the concentration of iodide ions in the precursor solution is within the range from about 0.01 to about 1.0 M.

16. The device of claim 14, further comprising a transport system arranged to transport at least one portion of the test solution from a test solution source to the device, from the device to an analyte detection system, or both.

17. The device of claim 14, further comprising an analyte detection system arranged to detect the starch-iodine complex in the test solution.

18. The device of claim 17, wherein the detection system comprises a light source, an optical cell and a light detector.

19. The device of claim 17, wherein the complex is detected by measuring the light absorbance of the test solution at one or more wavelengths.

20. The device of claim 19, wherein the one or more wavelengths is within the range of from about 400 nm to about 800 nm.

21. The device of claim 17, further comprising a measurement system arranged to quantify the amount of analyte detected by the device by quantifying the amount of starch-iodine complex.

22. A method for detecting at least one analyte in a test solution, the method comprising application of at least one quantity of electrical power between the at least one first electrode and the at least one second electrode of a device according to claim 21, thereby causing at least some of the at least one precursor compound to migrate from the at least one precursor solution to the at least one test solution, where it reacts electrochemically at or near the at least one first electrode to generate at least one reagent for detecting the at least one analyte.

23. The device of claim 14, wherein
- the cell separator inhibits mixing of the test solution and the precursor solution when the device is inactive, but permits transfer of iodide ions from the precursor solution to the test solution when the device is activated;
- the device is activated by an application of at least one quantity of electrical power between the anode and the cathode; and
- activation of the device permits at least some of the iodide ions to migrate from the precursor solution, through the cell separator, to the test solution, wherein the iodide ions are oxidized at the anode to produce iodine, and the iodine generated combines with the starch in the test solution to produce a starch-iodine complex.

* * * * *